United States Patent [19]
Mathies et al.

[11] Patent Number: 6,045,676
[45] Date of Patent: *Apr. 4, 2000

[54] ELECTROCHEMICAL DETECTOR INTEGRATED ON MICROFABRICATED CAPILLIARY ELECTROPHORESIS CHIPS

[75] Inventors: Richard A. Mathies, Moraga; Alexander N. Glazer, Orinda; Adam T. Woolley, Albany; Kaigin Lao, San Francisco, all of Calif.

[73] Assignee: The Board of Regents of the University of California, Oakland, Calif.

[ * ] Notice: This patent is subject to a terminal disclaimer.

[21] Appl. No.: 08/916,557

[22] Filed: Aug. 22, 1997

Related U.S. Application Data

[63] Continuation-in-part of application No. 08/703,394, Aug. 26, 1996, Pat. No. 5,906,723.

[51] Int. Cl.⁷ .................................................. G01N 27/26
[52] U.S. Cl. .......................................... 204/603; 204/601
[58] Field of Search ................................ 204/601–605, 204/451–455

[56] References Cited

U.S. PATENT DOCUMENTS

| | | | |
|---|---|---|---|
| 4,891,120 | 1/1990 | Sethi et al. | 204/299 R |
| 5,071,531 | 12/1991 | Soane | 204/182.8 |
| 5,126,022 | 6/1992 | Soane | 204/180.1 |
| 5,194,133 | 3/1993 | Clark et al. | 204/299 R |
| 5,429,734 | 7/1995 | Gajar et al. | 204/299 R |
| 5,580,435 | 12/1996 | Kovacs | 204/603 |

FOREIGN PATENT DOCUMENTS

| | | |
|---|---|---|
| 4314755 | 11/1994 | Germany . |
| WO95/10040 | 4/1995 | WIPO . |
| 98/09161 | 3/1998 | WIPO . |

OTHER PUBLICATIONS

Gavin, Peter F., et al.; "Continuous Separations with Microfabricated Electrophoresis–Electrochemical Array Detection",*J. Am. Chem. Soc.* (1996), vol. 118, pp. 8932–8936.

Adam T. Woolley, et al., Ultra–high–speed DNA fragment separations using microfabricated capillary array electrophoresis chips, Proc. Natl. Acad. Sci., vol. 91, pp. 11348–11352, Nov. 1994, Biophysics.

Mark K. Shigenaga, et al., In Vivo Oxidative DNA Damage . . . , Methods in Enzymology, vol. 186, pp. 521–530, 1994.

Dan Wu, et al., Electrophoretically mediated micro–assay of alkaline phosphatase using electrochemical and spectrophotometric detection in capillary electrophoresis, Journal of Chromatography D, 656 (1994) pp. 357–363.

Dean H. Johnston, et al., Electrochemical Measurement of the Solvent Accessibility of Nucleobases Using Electron Transfer between DNA and Metal Complexes, J. Am. Chem. Soc. 1995, 117, pp. 8933–8938.

Teresa M. Olefirowicz, et al., Capillary Electrophoresis in 2 and 5 μm Diameter Capillaries: Application to Cytoplasmic Analysis, Anal. Chem. 1990, 62, pp. 1872–1876.

Karin Pihel, et al., Electrochemical Detection of Histamine and 5–Hydroxytryptamine at Isolated Mast Cells, Anal. Chem. 1995, 67 pp. 4514–4521.

Fu–Ren F. Fan, et al., Electrochemical Detection of Single Molecules, Science, vol. 267, Feb. 10, 1995, pp. 871–874.

Shigeori Takenaka, et al., Electrochemically Active DNA Probes: Detection of Target DNA Sequences at Femtomole Level . . . , Analytical Biochemistry 218, (1994), pp. 436–443.

(List continued on next page.)

*Primary Examiner*—William H. Beisner
*Attorney, Agent, or Firm*—Flehr Hohbach Test Albritton & Herbert LLP

[57] ABSTRACT

A microfabricated capillary electrophoresis chip which includes an integral thin film electrochemical detector for detecting molecules separated in the capillary.

9 Claims, 12 Drawing Sheets

OTHER PUBLICATIONS

D. E. Smith, et al., Second Harmonic Alternating Current Polarography with a Reversible Electrode Process, Analytical Chemistry, vol. 33, No. 4, Apr. 1961, pp. 482–485.

Phillip D. Voegel, et al., Electrochemical detection with copper electrodes in liquid chromatography and capillary electrophoresis, American Laboratory, Jan. 1996, pp. 39–45.

Jonathan M. Slater, et al., On–chip Microband Array Electrochemical Detector for use in Capillary Electrophoresis, Analyst, Nov. 1994, vol. 119, pp. 2303–2307

Andrew G. Ewing, et al., Electrochemical Detection in Microcolumn Separations, Analytical Chemistry, vol. 66, No. 9, May 1, 1994, pp. 527A–536A.

Xiaohua Huang, et al., On–Column Conductivity Detector for Capillary Zone Electrophoresis, Analytical Chemistry, vol. 59, No. 23, Dec. 1, 1987, pp. 2747–2749.

Mei–Cheny Chen, et al., An Electrochemical Cell for End–Column Amperometric Detection in Capillary Electrophoresis, Analytical Chemistry, vol. 67, No. 21, Nov. 1, 1995, pp. 4010–4014.

Thomas J. O'Shea, et al., Capillary electrophoresis with electrochemical detection employing an on–column Nafion joint, Journal of Chromatography, 593, (1992), pp. 309–312.

Adam T. Woolley, et al., Ultra–High Speed DNA Sequencing Using Capillary Electrophoresis Chips, Anal. Chem. 1995, 67, pp. 3676–3680.

FIG_1
(PRIOR ART)
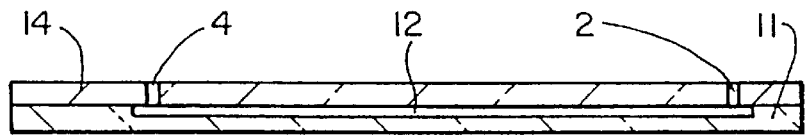
FIG_2
(PRIOR ART)
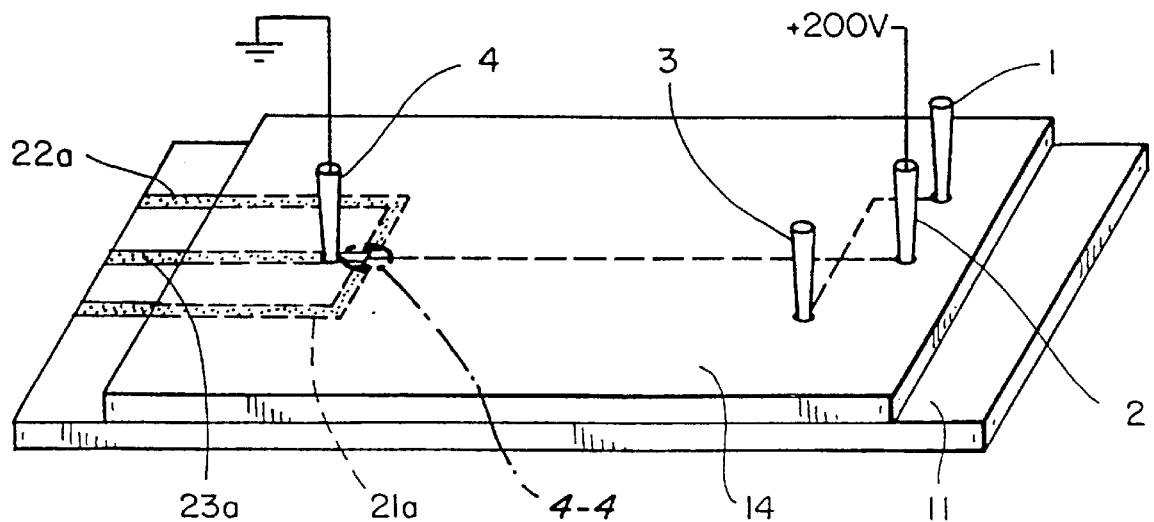
FIG_3

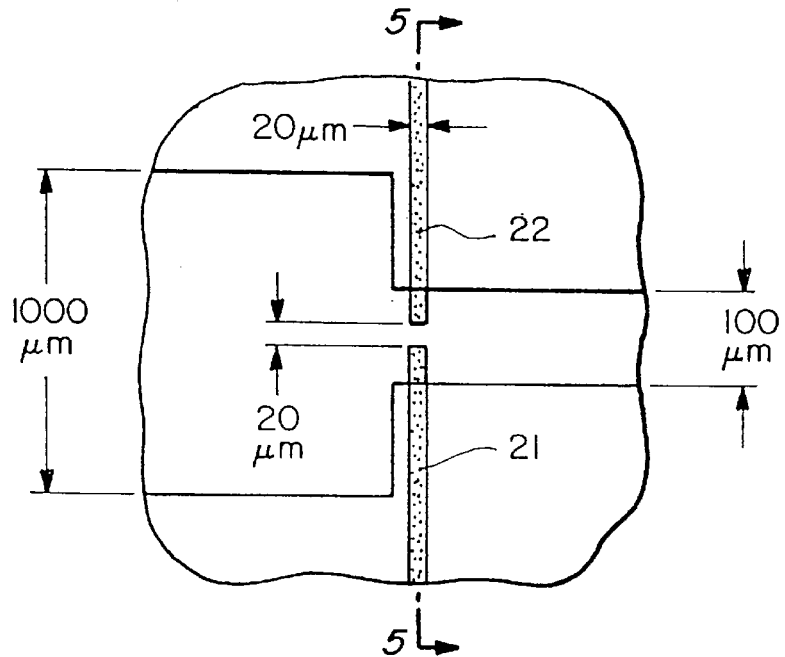
FIG_4
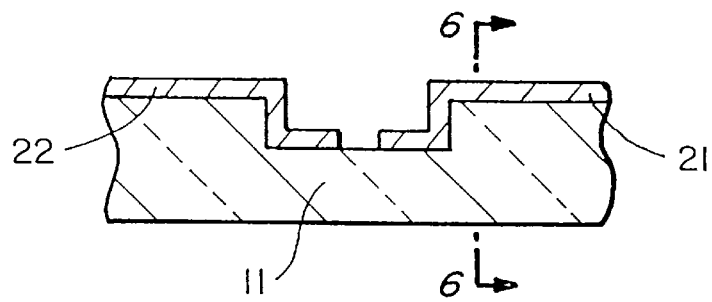
FIG_5
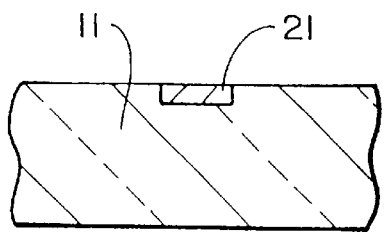
FIG_6

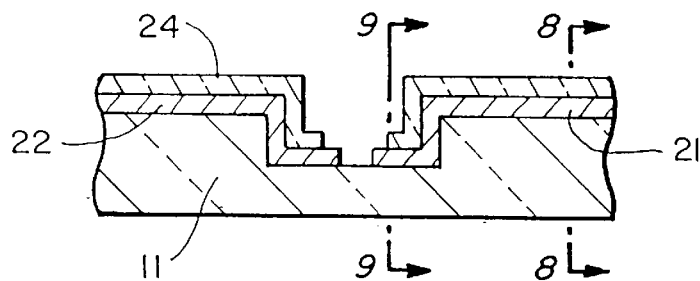
FIG_7
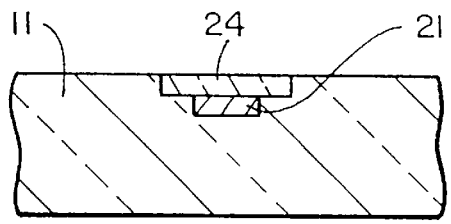
FIG_8
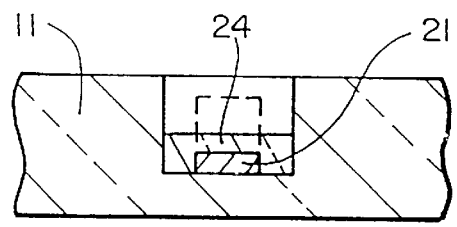
FIG_9
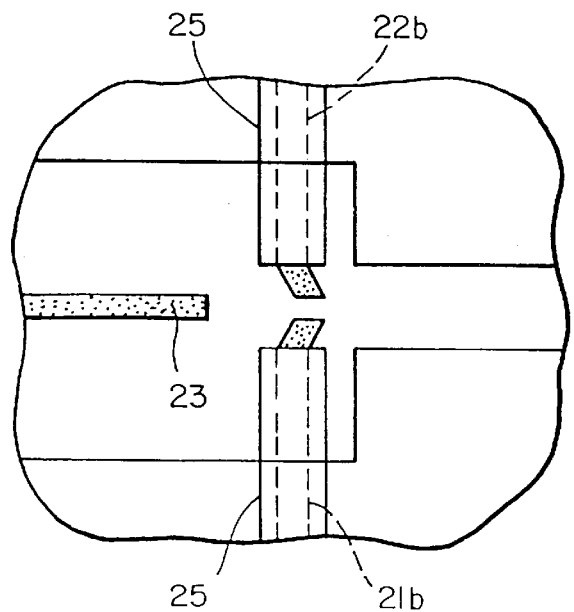
FIG_10

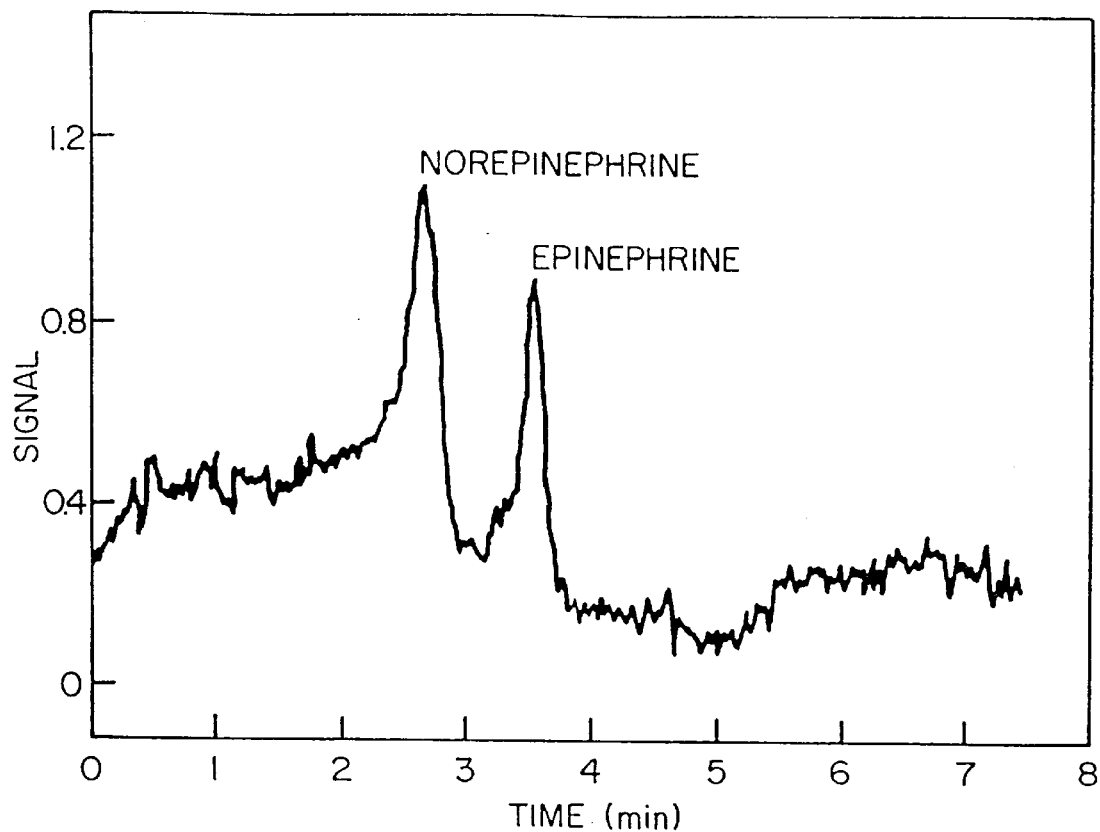
FIG_11
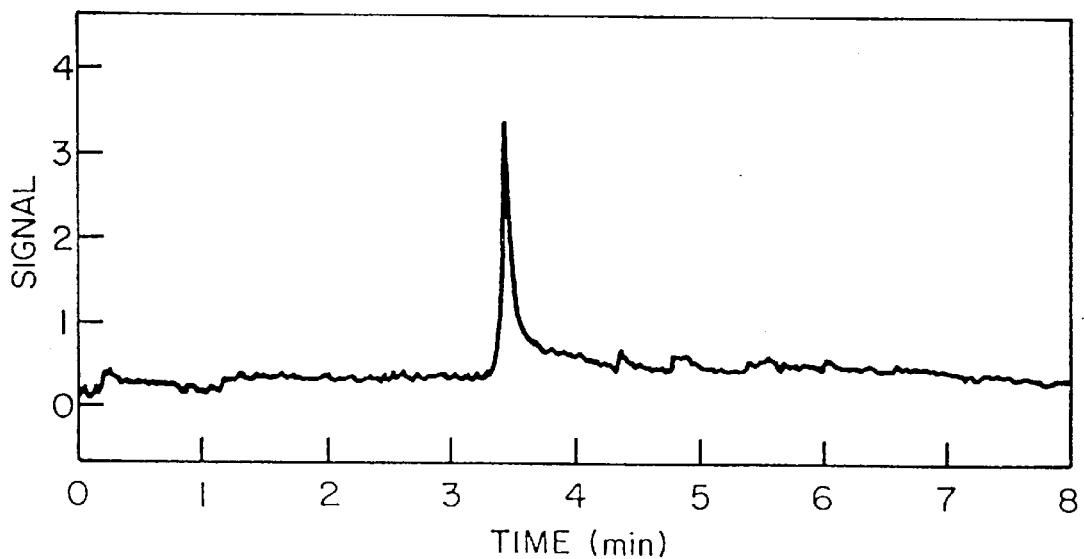
FIG_12A

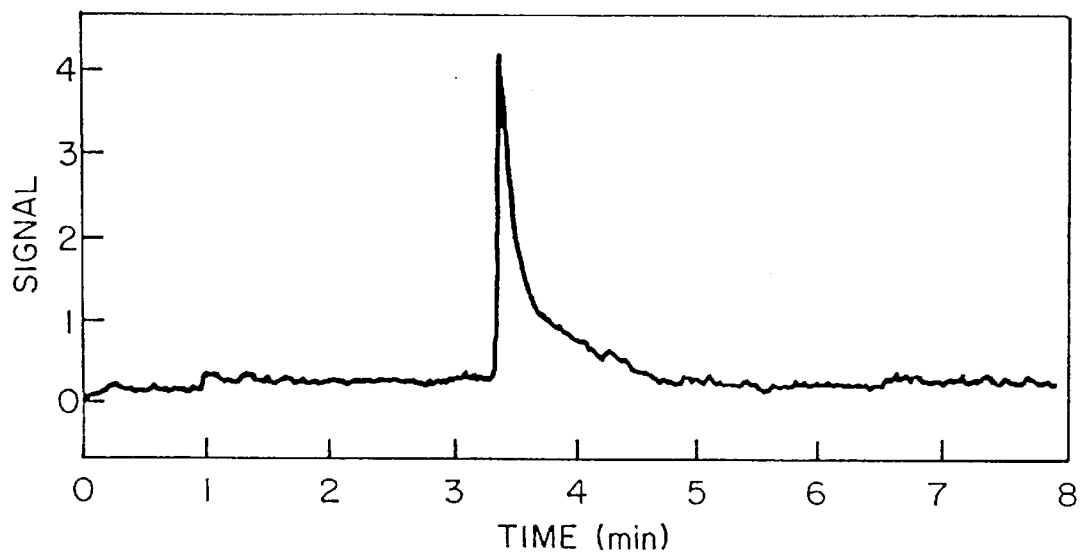
FIG_12B
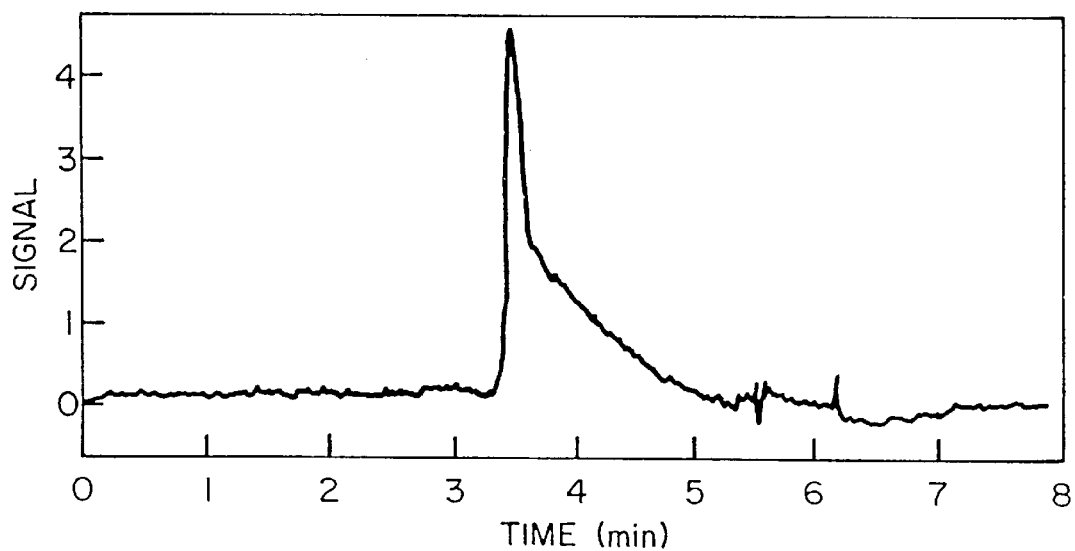
FIG_12C

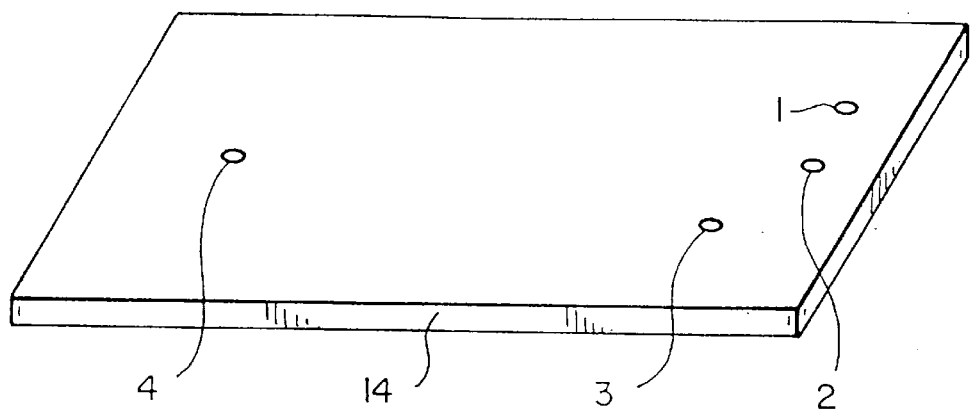
FIG_13A
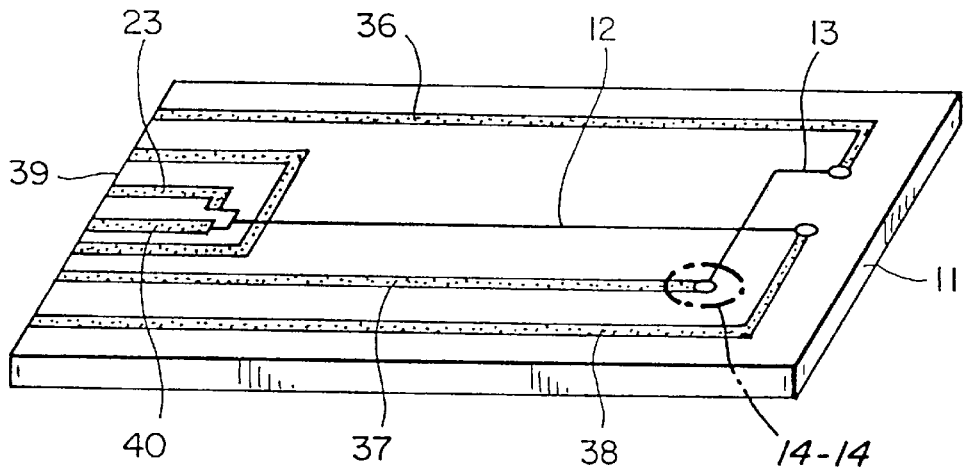
FIG_13B
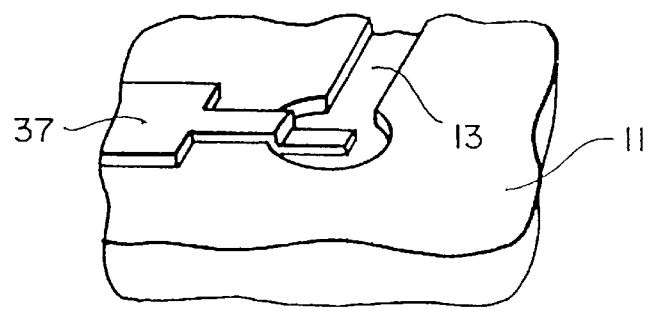
FIG_14

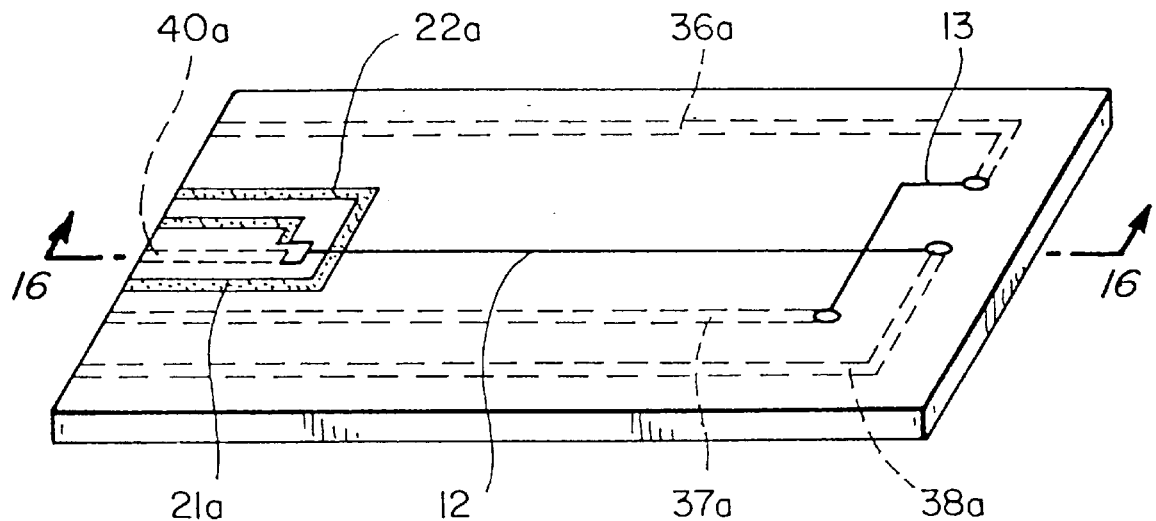
FIG_15
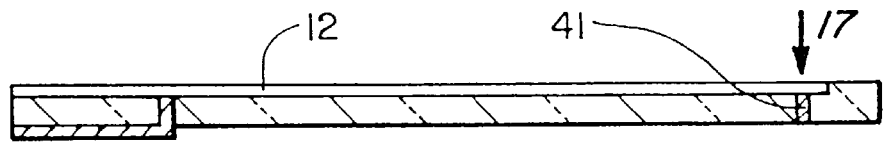
FIG_16
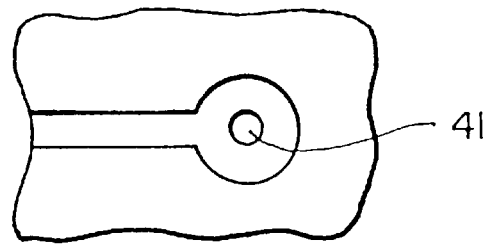
FIG_17

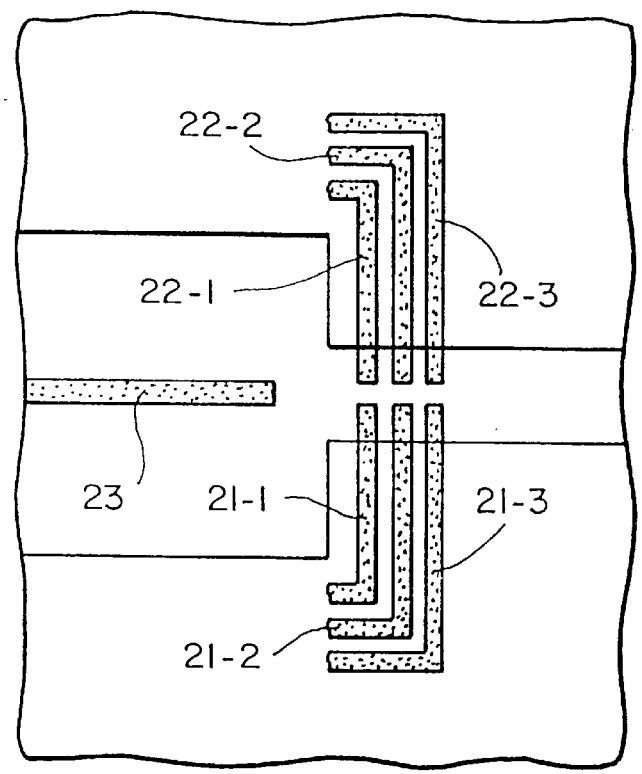
FIG_18
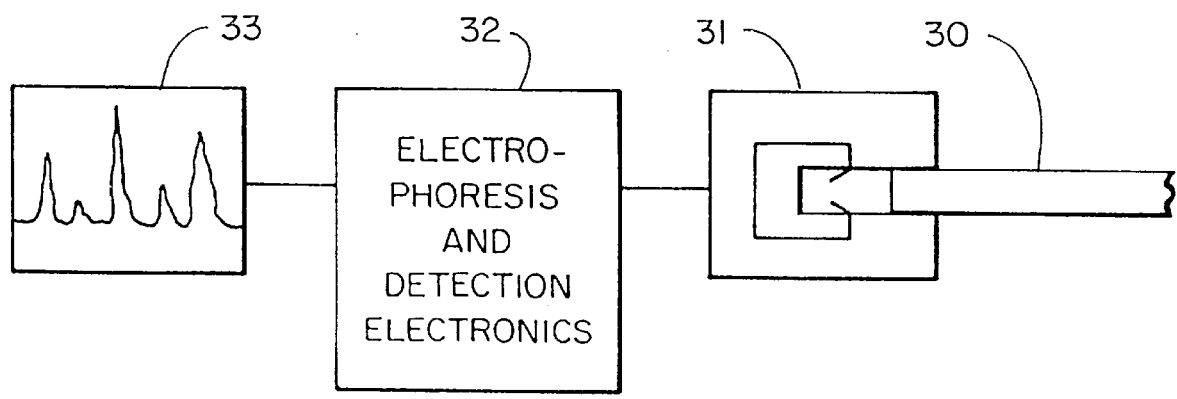
FIG_19

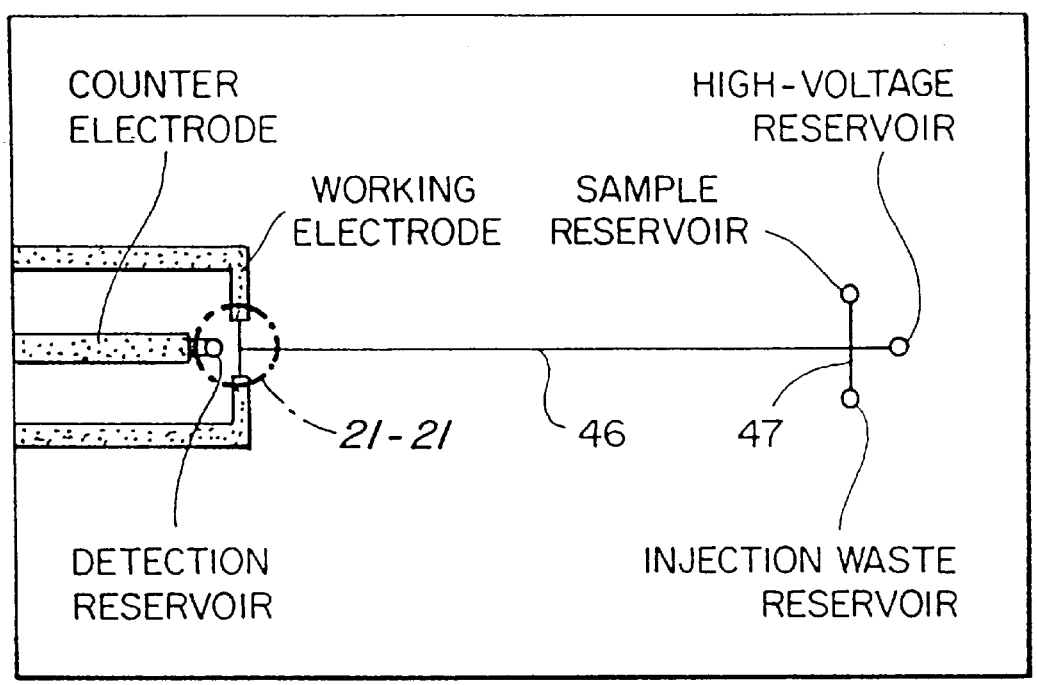
FIG_20
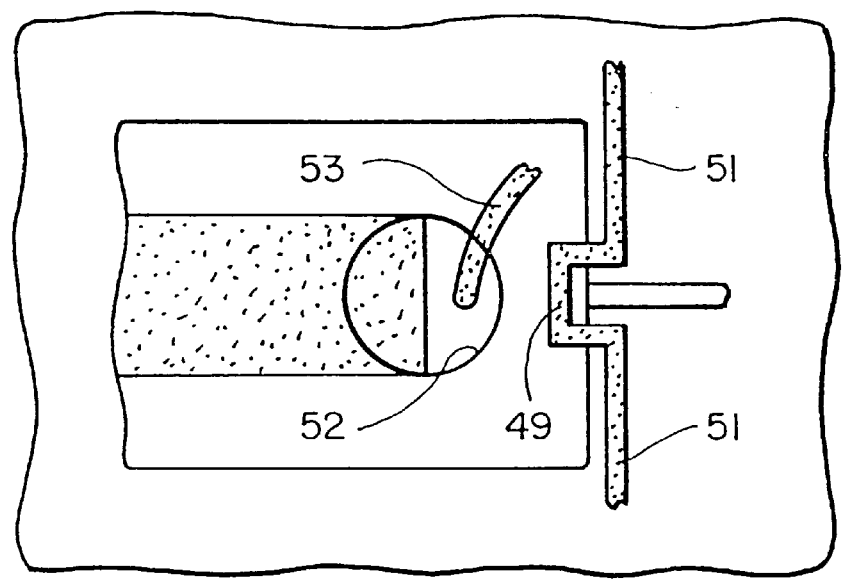
FIG_21

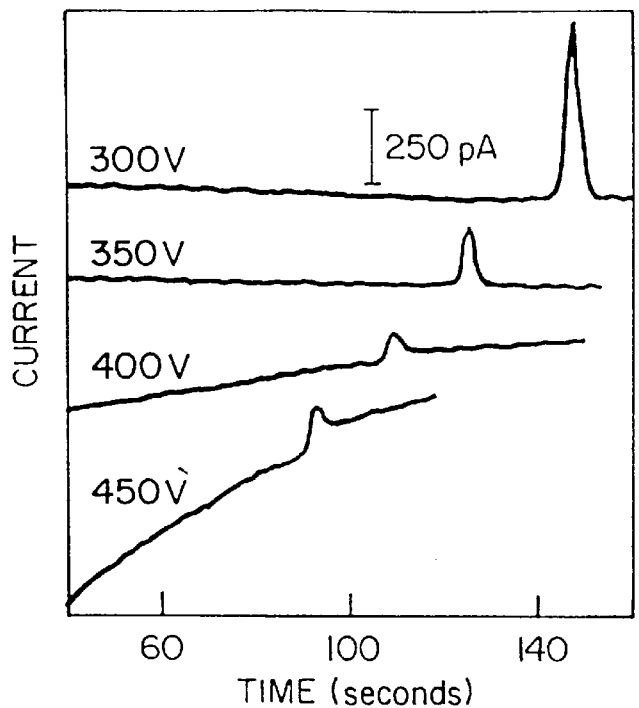
FIG_22
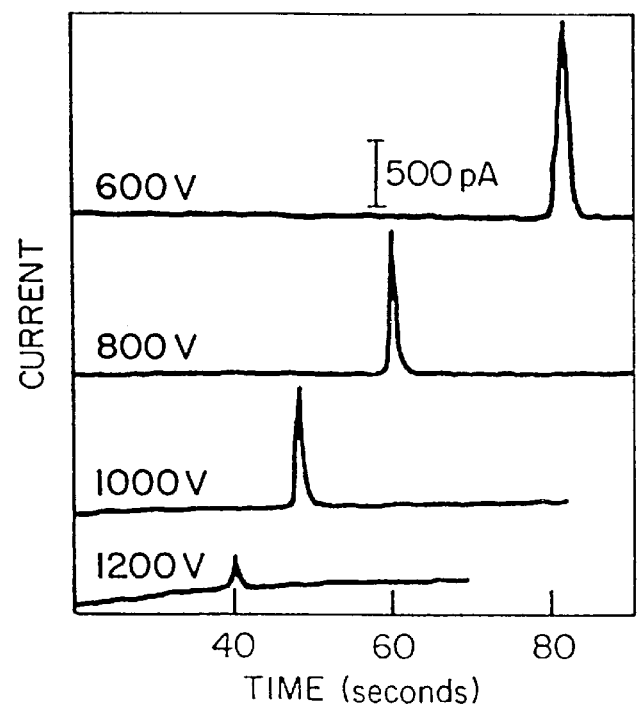
FIG_23

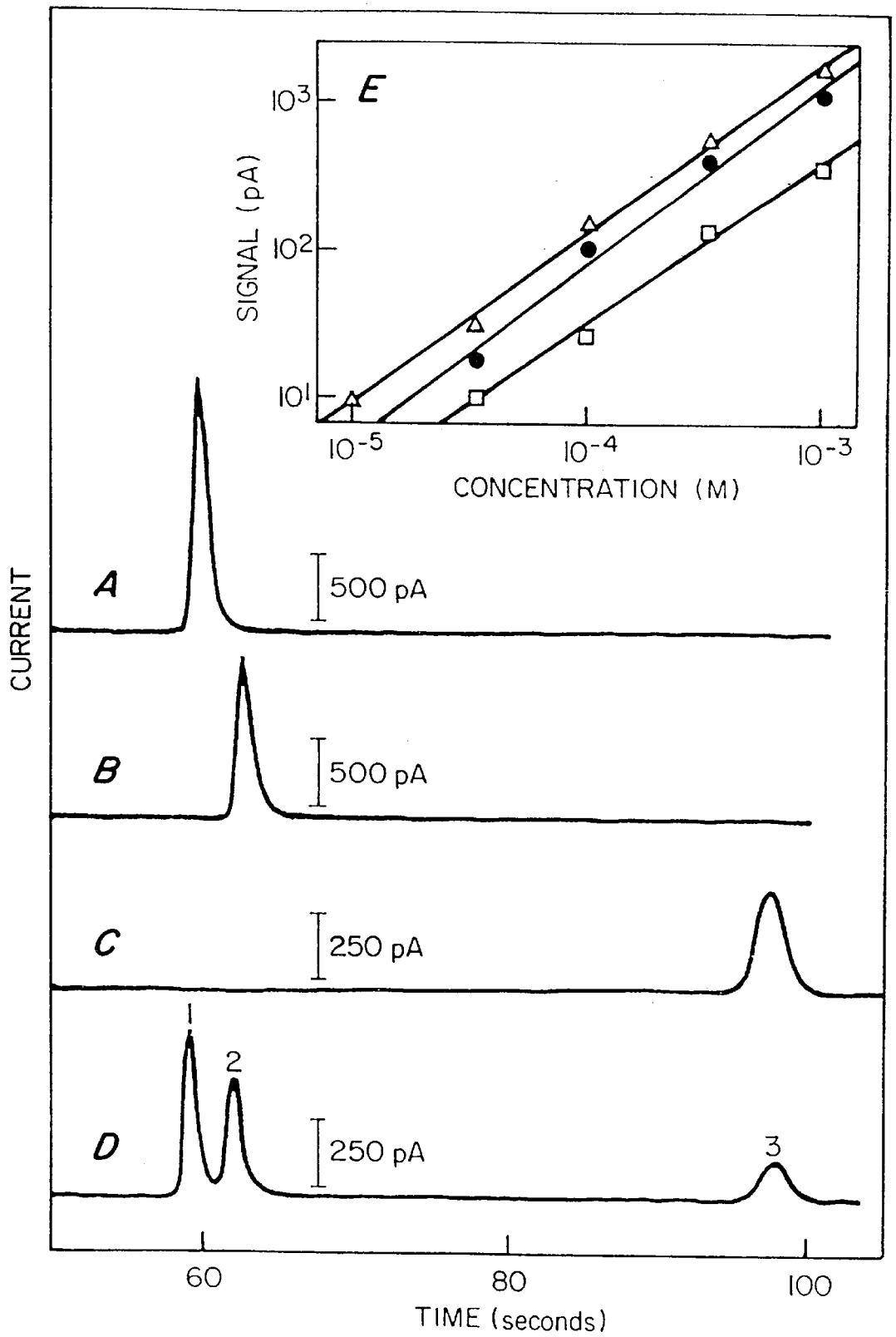
FIG_24

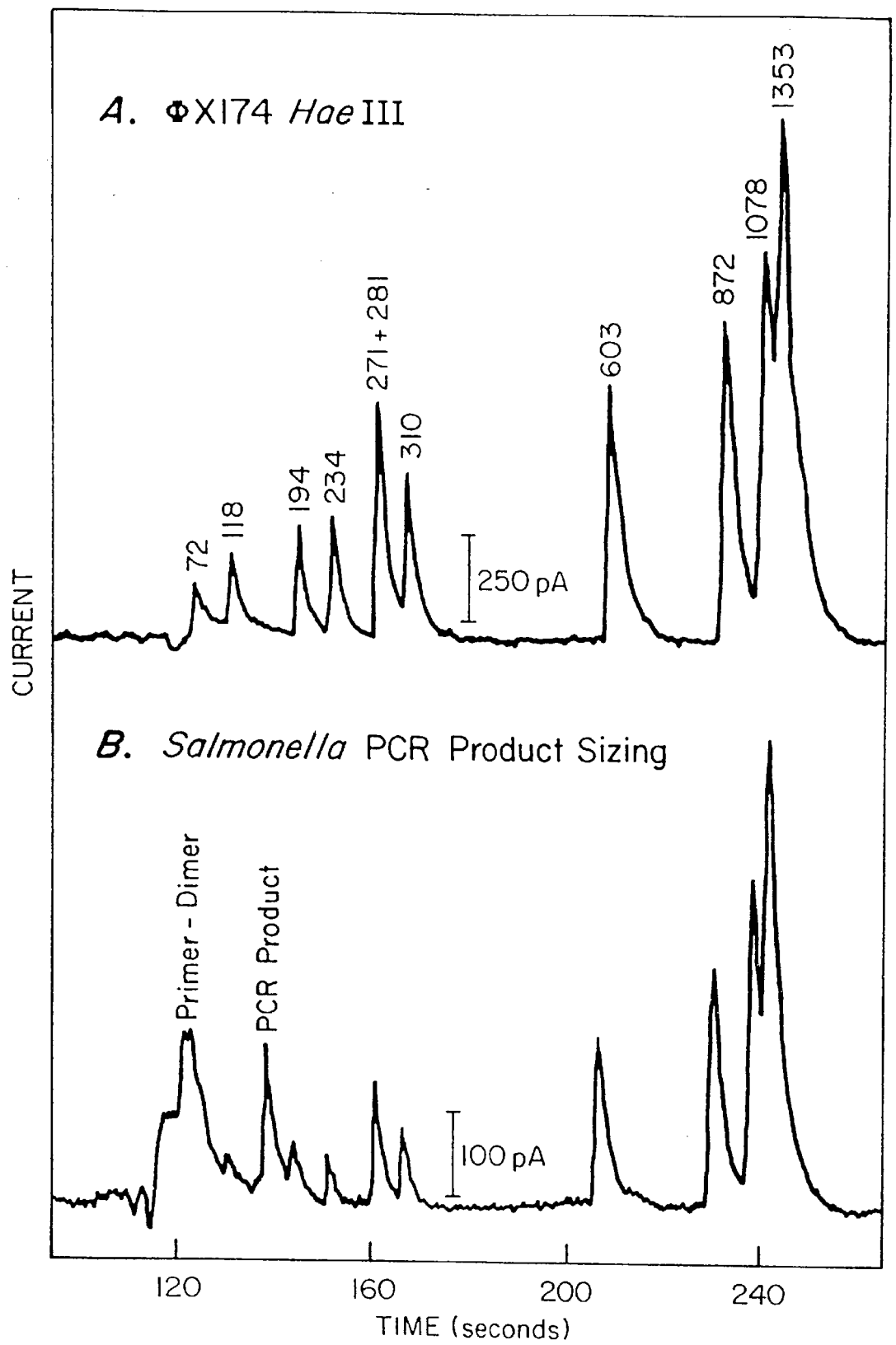
FIG_25

ELECTROCHEMICAL DETECTOR INTEGRATED ON MICROFABRICATED CAPILLIARY ELECTROPHORESIS CHIPS

RELATED APPLICATION

This application is a continuation-in-part of Ser. No. 08/703,394 filed Aug. 26, 1996, now U.S. Pat. No. 5,906,723.

BRIEF DESCRIPTION OF THE INVENTION

This invention relates generally to an electrochemical detector as a component of an integrated separation and detection module on a microfabricated capillary electrophoresis chip and to a method of fabricating the electrochemical detector and more particularly to the design of a thin film electrochemical detector which can be precisely positioned in a microfabricated capillary.

BACKGROUND OF THE INVENTION

Electrochemical detection has been employed in liquid chromatography and in capillary electrophoresis (CE). It has been demonstrated that electrochemical detection is very sensitive and can measure $10^{-16}$ to $10^{-19}$ moles of sample with typical detection volumes from nL to pL (Ewing, A. G.; Mesaros, J. M.; Gavin, P. F., Electrochemical Detection in Microcolumn Separations, Anal. Chem., 66, 527A–536A, (1994); Voegel, P. D.; Baldwin, R. P., Electrochemical Detection with Copper Electrodes in Liquid Chromatography and Capillary Electrophoresis, American Laboratory, 28(2), 39–45, (1996)). Electrochemical methods have also been used to detect DNA (Shigenaga, M. K.; Park, J.-W.; Cundy, K. C.; Gimeno, C. J.; Ames, B. N., In Vivo Oxidative DNA Damage: Measurement of 8-hydroxy-2'-deoxyguanosine in DNA and Urine by High-Performance Liquid Chromatography with Electrochemical Detection, Methods in Enzymol., 186, 521–530, (1990); Takenaka, S.; Uto, H.; Knodo, H.; Ihara, T.; Takagi, M., Electrochemically Active DNA Probes-Detection of Target DNA Sequences at Femtomole Level by High-Performance Liquid Chromatography with Electrochemical Detection, Anal. Biochem., 218, 436–443, (1994); Johnston, D. H.; Glasglow, D. C.; Thorp, H. H., Electrochemical Measurement of the Solvent Accessibility of Nucleobases Using Electron Transfer Between DNA and Metal Complexes, J. Am. Chem. Soc., 117, 8933–8938, (1995)), single cells (Olefirowicz, T. M.; Ewing, A. G., Capillary Electrophoresis in 2 and 5 $\mu$M Diameter Capillaries: Application to Cytoplasmic Analysis, Anal. Chem., 62, 1872–1876, (1990); Pihel, K.; Hsieh, S.; Jorgenson, J. W.; Wightman, R. M., Electrochemical Detection of Histamine and 5-Hydroxytryptamine at Isolated Mast Cells, Anal. Chem., 67, 4514–4521, (1995)), and even single molecules (Fan, F.-R. F.; Bard, A. J., Electrochemical Detection of Single Molecules, Science, 267, 871–874, (1995)). The operation of these electrochemical detectors is typically based on the use of three electrodes called the working, counter, and reference electrodes. There are three configurations which have been used to detect CE separations: on-column (Huang, X.; Pang, T.-K. J.; Gordon, M. J.; Zare, R. N., On-Column Conductivity Detector for Capillary Zone Electrophoresis, Anal. Chem., 59, 2747–2749, (1987), where the electrodes of the detector are placed within the capillary; end-column (Huang, X.; Zare, R. N.; Sloss, S.; Ewing, A. G., End-Column Detection for Capillary Zone Electrophoresis, Anal. Chem., 63, 189–192, (1991); Chen, M.-C.; Huang, H.-J., An Electrochemical Cell for End-Column Amperometric Detection in Capillary Electrophoresis, Anal. Chem., 67, 4010–4014, (1995)), where the electrodes are placed directly at the end of the separation capillary; and off-column (Olefirowicz, T. M.; Ewing, A. G., Capillary Electrophoresis in 2 and 5 $\mu$M Diameter Capillaries: Application to Cytoplasmic Analysis, Anal. Chem., 62, 1872–1876, (1990); O'Shea, T. J.; Greenhagen, R. D.; Lunte, S. M.; Lunte, C. E.; Smyth, M. R.; Radzik, D. M.; Watanabe, N., Capillary Electrophoresis with Electrochemical Detection Employing an On-Column Nafion Joint, J. Chromatogr., 593, 305–312, (1992); Wu, D.; Regnier, F. E.; Linhares, M. C., Electrophoretically Mediated Micro-Assay of Alkaline Phosphatase using Electrochemical and Spectrophotometric Detection in Capillary Electrophoresis, J. Chromatogr. B, 657, 357–363, (1994)), where the electrodes are electrically isolated from the electrophoresis voltage by a grounded porous glass tube. On-column electrochemical detection of CE separations has been performed by fixing two platinum wires through diametrically opposed holes drilled by a laser in a capillary tube. This structure is very difficult to manufacture and align, and the placement of the detection electrodes within the high voltage region of the separation column is problematic. In this format, one is trying to detect small currents or voltages while applying many kV to the separation column. The mechanical instability and poor definition of the electrode alignment can lead to significant electrical pickup or fluctuation in the background, making the desired signal very difficult to detect. The presence of high voltage gradients and significant electrophoretic currents in the column near the electrodes can induce stray signals. The end-column and off-column detection formats are important because they minimize the influence of the electrophoresis voltage. In the end-column format, one wants to place the detection electrodes as close to the end of the electrophoresis channel as possible so the detection is performed as close to ground potential as possible. This is very difficult to do with conventional manufacturing techniques. The electrodes must be placed with micron precision at the end of the capillary. Any error in the placement will cause loss of analyte signal if the electrodes are too far from the opening or high voltage pick up if the electrodes are placed within the separation column. Furthermore, fluctuations in electrode placement or electrode-electrode gap can cause severe fluctuations in the background signal producing noise. Typically, one must use micromanipulators and a microscope to assemble the detector. Furthermore, the engineering of the electrical isolation by connection of the separation and detection capillary tubes with a grounded porous glass tube in the off-column format is rather difficult to assemble and operate, and the junction can be mechanically unstable and poorly defined. In one case, although Slater and Watt (Slater, J. M.; Watt, E. J., On-chip Microbond Array Electrochemical Detector for use in Capillary Electrophoresis Analyst, 1994, 119, 2303–2307) photolithographically fabricated electrodes on a substrate, because they did not make a fully integrated separation and detection device, they were forced to use said undesirable junctions to couple their detector to a conventional cylindrical capillary.

There is a need for a microfabricated capillary electrophoresis chip with integral thin film electrochemical detector and electrophoresis leads which can be easily connected to associated electrical electrophoresis and detector apparatus.

OBJECTS AND SUMMARY OF THE INVENTION

It is a general object of the present invention to provide an electrochemical detector for capillary electrophoresis on a microfabricated planar glass chip that overcomes the aforementioned short comings of the prior art.

It is another object of the present invention to provide a microfabricated capillary electrophoresis chip with a microelectrochemical detector that minimizes the effect of interference from applied electrophoresis fields.

It is another object of the present invention to provide detector electrodes which are reproducibly, accurately and conveniently placed, robust and sensitive.

It is a further object of the present invention to provide detector electrodes which are precisely and stably positioned at the very end of the capillary where they are close to ground potential and thereby immune to pick up from the high electrophoresis potentials.

It is a further object of the present invention to provide a microfabricated capillary electrophoresis chip with integrated thin film electrochemical detector electrodes and electrophoresis electrodes which can be produced accurately and at low cost.

The foregoing and other objects of the invention are achieved by integrating an electrochemical detector on a microfabricated capillary electrophoresis chip of the type including a substrate having at least an elongated separation channel and a cover plate bonded to said substrate to form with said channel a separation capillary. A thin film electrochemical detector is fabricated on the surface of said substrate or cover plate with thin narrow electrodes extending into said channel near one end of said channel.

BRIEF DESCRIPTION OF THE DRAWINGS

The foregoing and other objects of the present invention will be more clearly understood from the following description when read in conjunction with the accompanying drawings, of which:

FIG. 1 shows a microfabricated capillary electrophoresis chip in accordance with the prior art;

FIG. 2 is a sectional view taken along the line 2—2 of FIG. 1;

FIG. 3 is a perspective view of a microfabricated capillary electrophoresis chip incorporating the present invention;

FIG. 4 is an enlarged view of the indicated detector region 4—4 of FIG. 3;

FIG. 5 is a sectional view taken along the line 5—5 of FIG. 4;

FIG. 6 is a sectional view taken along the line 6—6 of FIG. 5;

FIG. 7 is a sectional view showing another embodiment of the electrochemical electrodes shown in FIGS. 3 and 4;

FIG. 8 is a sectional view taken along the line 8—8 of FIG. 7;

FIG. 9 is a sectional view taken along the line 9—9 of FIG. 7;

FIG. 10 is an enlarged view of another detector embodiment;

FIG. 11 is an electropherogram of norepinephrine and epinephrine separated on a capillary electrophoresis chip with integrated electrochemical detection;

FIGS. 12A–12C are electropherograms of norepinephrine separations obtained with a capillary electrophoresis chip with integrated electrochemical detection for three consecutive experiments;

FIGS. 13A–13B are perspective views of a microfabricated capillary electrophoresis chip with integrated electrochemical detection including thin film connections to the separation and injection channels;

FIG. 14 is an enlarged view of the section 14—14 of FIG. 13B;

FIG. 15 is a perspective view of a substrate including an integrated electrochemical detector and leads connected to the injection and separation channels;

FIG. 16 is a sectional view taken along the lines 16—16 of FIG. 15;

FIG. 17 is an enlarged view taken along the direction of arrow 17 of FIG. 16;

FIG. 18 is a partial enlarged view showing a plurality of electrochemical detection electrodes formed along the separation channel;

FIG. 19 is a block diagram of an apparatus for joining a capillary electrophoresis chip into an overall electrochemical separation and analysis system in accordance with the present invention.

FIG. 20 is a plan view of a microfabricated fabricated capillary electrophoresis chip in accordance with another embodiment of the present invention.

FIG. 21 is an enlarged view of the area 21—21 of FIG. 20 showing the detection electrode and reference electrode.

FIG. 22 and 23 show the effect of the separation distance between the working electrode and the reference electrode.

FIG. 24 shows capillary electrophoresis separations and detection of neurotransmitters.

FIG. 25 shows the separation and detection of DNA in a chip using indirect electrochemical detection.

DESCRIPTION OF PREFERRED EMBODIMENTS

FIGS. 1 and 2 show a microfabricated capillary electrophoresis (CE) chip formed in accordance with the prior art. The capillary channels are formed on an etched glass substrate 11 by photolithography and chemical etching. The process is described by Woolley et al., Ultra-High-Speed DNA Fragment Separations Using Microfabricated Capillary Array Electrophoresis Chips, Proc. Nat'l. Acad. Sci., USA, 91, 11348–11352 (1994). The separation channel 12 and the injection channel 13 for injecting sample into the channel by stack or plug injection are described in the above reference. In one example, all channels were etched to a depth of 8 $\mu$m; the separation channels were 100 $\mu$m wide, and the injection channels were 50 $\mu$m wide. The separation channels were 46 mm long, with a distance of 39 mm from the point of injection to the electrochemical detector. The injection channels were 22 mm long with a distance of 12 mm from the point of sample introduction to the injection region. A top plate 14 was bonded to the etched glass substrate to form the capillaries which are filled with a separation matrix. The top plate includes drilled holes 1–4 which provide reagent reservoirs to the ends of the separation channel and the ends of the injection channel.

In the prior art, the electrophoretic DNA separations in the microfabricated capillary channels were detected by bulky, inconvenient and costly systems employing external lasers, optical systems, photomultiplier tubes, etc. It has thus far not been possible to integrate the optical detection system onto a microfabricated CE chip. Similarly, although electrochemical detection of conventional capillary electrophoresis separations performed in hollow silica capillaries has been performed with a variety of external electrode and detector formats, such a detector has never been integrated within a CE electrophoresis chip system with a single microfabrication technology.

In accordance with one embodiment of the present invention, platinum electrodes for electrochemical detectors are fabricated on the substrate or top plate by RF sputtering and photolithography before the top or cover plate is bonded to the etched substrate. The electrodes can be accurately positioned at the ends of the separation column where they are close to ground potential thereby providing a stable, easy to manufacture, inexpensive electrochemical detector. Other suitable electrode materials are gold, chromium, carbon and other relatively inert easily deposited conductive materials.

Referring to FIGS. 3–6, a CE chip is shown with thin film platinum electrodes. The electrodes comprise a reference electrode 21, a working electrode 22, and a counter electrode 23 (not shown) connected to an external circuit by thin film conductors 21a, 22a and 23a. The substrate is preferably etched so that the electrodes and thin film conductors are inset as shown in FIG. 6 whereby the top plate 14 can be effectively sealed to the substrate. The reference and working electrodes include a narrow portion extending into the channel with the ends separated and adapted to detect current or voltage as molecules undergo redox reactions or conduct current as they migrate past the spaced electrodes. The electrodes are connected to wider thin film leads 21a, 22a and 23a which extend to the edge of the chip for insertion into a connector (not shown) to provide electrical connection to the electrical measuring circuits. In order to limit the exposed area of the narrow portions of the working and reference electrodes which extend into the channel, the electrodes can be covered with an insulating dielectric film such as $SiO_2$. This is illustrated in FIGS. 7–9 where the electrodes 21 and 22 are covered by an insulating film 24. In one example, the Pt electrodes were deposited using RF sputtering; the thickness of the electrodes was 3000 Å. The working and reference electrodes were 20 $\mu$m wide Pt electrodes that were precisely aligned on opposite sides of the channel (to minimize the potential difference between electrodes) and extended 40 $\mu$m into the channel, with a spacing of 20 $\mu$m (see FIG. 4). The 100 $\mu$m channel widens to 1000 $\mu$m at the end to increase the volume of the separation channel. The working and reference electrodes were placed 20 $\mu$m from the point of widening. The counter electrode was 2 mm wide and extended into the widened portion at the end of channel. The advantage of this design is that it minimizes the influence of the electrophoresis voltage by working very close (20 $\mu$m) to the ground end of the channel where the analyte is still highly concentrated, while still performing on-column detection. After careful alignment, the etched bottom plate or substrate 11 with the Pt electrodes was thermally bonded to a top glass plate 14 with 0.8 mm holes 1–4. The detector electrodes can also be formed adjacent the end of the channel as shown in FIG. 10. The detector electrodes 21b and 22b are covered by an insulating film 25 with the ends exposed. Although specific dimensions have been given for the described embodiment, the channel width and depth can be between 1–2000 $\mu$m, the electrode width 1–2000 $\mu$m and the electrode spacing 1–5000 $\mu$m but preferably the channel width and depth is between 1–500 $\mu$m, the electrode width is 1–500 $\mu$m, and the electrode spacing is between 1–500 $\mu$m.

The advantages of such fabrication and design are that (i) the working and reference electrodes can be easily and precisely positioned near, at, or just beyond the opening of the separation channel where pickup and interference from the electrophoresis voltage is minimal and where the analyte concentration in the separated zone is still high. This precise (micron) alignment is only possible with an integrated microfabricated device. (ii) The electrodes in the channel are very small in the electrophoresis dimension. This is advantageous because it facilitates the placement of multiple electrodes, FIG. 18, at essentially (compared to the zone size) the same point in the channel. It is also advantageous because we have observed that wider electrodes tend to nucleate electrolysis bubbles presumably because they sample more of the electrophoretic voltage gradient. This effect can be reduced by covering the body of the electrode (not the tip) with an insulating layer. Such thin electrodes can only be produced via photolithography on an integrated device. Finally, one wants to have a precise and small electrode gap so that each detector functions the same and has a similar sensitivity and probed volume. The ability to fabricate a small gap will produce low backgrounds because the effective volume of conductive and capacitive solution between the electrode is small. The ability to make detectors with small gaps is also advantageous because it permits the fabrication and detection of narrow separation channels which require only small amounts of sample and which have very high electrophoretic resolution.

It is noted that the channel widens at the end just past or at the point of detection. This is important because it keeps the first zones in the separation from raising the background as a result of diffusion of analyte back into the detector zone. By having a larger channel beyond the detector to provide a greater volume, the early zones are effectively diluted by the large solution volume around the counter electrode thereby keeping them from raising the background for the detection of subsequent bands. The wide section also has a low resistance because of its large cross section. This means that the voltage drop from the detector to the counter electrode will be much smaller thereby further reducing stray voltages at the detector and pickup and background. It will be appreciated that in addition to widening the channel to provide a greater volume, the depth may be increased.

Capillary zone electrophoresis separation of two neurotransmitters, epinephrine and norepinephrine was performed using a CE microchip having the dimensions given in the above examples following in general the methods outlined in Woolley et al Woolley, A. T.; Mathies, R. A., Ultra-High-Speed DNA Fragment Separations Using Microfabricated Capillary Array Electrophoresis Chips, Proc. Nat'l. Acad. Sci., USA, 91, 11348–11352, (1994); Woolley, A. T.; Mathies, R. A., Ultra-High-Speed DNA Sequencing Using Capillary Electrophoresis Chips, Anal. Chem., 67, 3676–3680, (1995)). A 30 mM solution of 2-(N-morpholino) ethanesulfonic acid (MES) adjusted to pH 5.6 with NaOH and modified with 20% (v/v) 2-propanol was used as the buffer. Stock solutions (10 $\mu$M) of epinephrine and norepinephrine (Sigma, St. Louis) were prepared in 0.01 M perchloric acid. Samples were serially diluted to the desired concentration in MES buffer. After placing the sample in reservoir 3, the samples were injected by applying 90 V/cm between reservoirs 1 and 3 (FIG. 3) for 20 seconds and the approximate injection volume was calculated as 40 pL. Separations were performed by applying 45 V/cm between reservoirs 2 and 4. The electrophoresis currents were typically 0.3 $\mu$A.

A Macintosh computer equipped with a National Instruments NB-MIO-16XL-18 I/O board was used to set voltages, store data and control the home-built three electrode potentiostat. The working electrode 22 was biased at +0.5 V relative to the reference electrode 21; the counter electrode 23 was used to complete the circuit. The potentiostat measured the current generated by molecules undergoing redox reactions as they migrated past the gap between the reference and working electrodes. Small currents (<1 pA could be detected even in the presence of the larger DC electrophoresis current (0.3 μA) in the channels. Alternatively, the small currents could be detected by biasing the working electrode with an AC potential (Smith, D. E.; Reinmuth, W. H., Second Harmonic Alternating Current Polarography with a Reversible Electrode Process, Anal. Chem., 33, 482–485, (1961)). A lock-in amplifier could then be used to distinguish the signal from the DC electrophoresis current. Prior to experiments, the electrodes were cleaned using 1M $H_2SO_4$ with a sine wave potential ($V_{p-p}$=0.5V) applied to the electrodes for 20 minutes.

FIG. 11 shows the separation of two neurotransmitters, epinephrine and norepinephrine, performed on the microfabricated CE chip with integrated electrochemical detection. Norepinephrine and epinephrine were detected at 2.6 min and 3.4 min, respectively, and the peaks were baseline resolved. The separation time was short, approximately 3 minutes.

FIGS. 12A–12C present the injection and detection of 0.48 nM epinephrine in three consecutive times. The reproducibility of migration times for these runs is excellent. The reproducibility of the signal strength is within a factor of 1.5, and most of the variability can be attributed to tailing from the later injections.

In addition to the use of thin film detection electrodes, thin film connections can be made from the edge of the chip to the ends of the separation and injection channels, 12 and 13. This would then permit insertion of the chip 30 into the socket 31, (FIG. 19,) which provides electrical connection to electrophoresis and detection electronics 32, for example, a processor of the type described above. The processor can be used to control stack or plug injection of sample into the separation channel and to apply electrophoresis voltages to the separation channel. Furthermore, the processor can apply voltages to the detector and analyze redox currents to provide a display or printout 33.

Referring to FIGS. 13 and 14, thin film leads 36, 37, and 38 are shown connected to the ends of the injection channel and to one end of the separation channel or column. A thin film connection 40 to the other end of the channel is also shown. The thin film leads terminate at the edge 39 of the substrate. The thin film leads are carefully placed in all the reservoirs so that they are far from the end of the channels so that hydrolysis bubbles due to current flow at the lead do not enter the adjacent channel. This is illustrated in FIG. 14 for one end of the injection channel. The chip can then be inserted into the socket for carrying out sample analysis. After the thin film leads are formed by photolithography and sputtering, the cover 14 is bonded to the substrate spaced from the end so that the leads can be contacted.

In another example, thin film leads 36a, 37a, 38a and 40a can be formed at the bottom of the substrate, FIGS. 15–17 with lead through connections 41 to the bottom of the etched channels and spaced from the ends of the channel.

Discrimination between species with different half-cell potentials can be achieved by sweeping over different bias voltages at the working electrode or by using multiple pairs of working and reference electrodes 21-1, 21-2 and 21-3, and 22-1, 22-2 and 22-3 at multiple bias voltages as shown in FIG. 18.

The design of another capillary electrophoresis (CE) chips with integrated electrochemical detection is presented in FIGS. 20 and 21. The separation channel and injection channel capillaries 46, 47 were microfabricated using standard photolithography, wet chemical etching, and thermal bonding methods. FIG. 21 shows the photolithograpically defined channel pattern used to minimize the effect of the separation electric field on electrochemical detection. The separation channel widened from ≈50 μm to 1000 μm just before the working electrode 49; the decreased resistance of the exit channel lowered the electric field in the detection region. A 10 μm wide thin film working electrode 49 had dual thin film leads 51 formed on the surface of the substrate and extending down the edge of the exit channel to connect to the ends of the electrode 49. The electrode was spaced 30 μm into the 1 mm wide exit channel. Microfabrication technology is particularly advantageous for this chip design because it allows facile, precise and stable placement of the working electrode 49 in the exit channel just beyond the end of the separation channel. As explained with respect to the embodiment of FIG. 10, positioning of the working electrode in the exit channel decouples the detector from the electrophoresis voltage and eliminates the problem of electrolysis in the separation channel.

A reference electrode 53 is placed in the access hole 52. It is obvious that this electrode can be a thin film electrode formed on the bottom or top of the exit channel. The spacing between the working electrode 49 and the access hole 52 has a substantial effect on the performance of the integrated electrochemical detector. FIGS. 22 and 23 show the effect of the distance from the access hole to the working electrode on separations. In FIG. 22 the edge of the access hole was 600 μm from the working electrode and electrophoretic separations of 1 mM dopamine at 300, 350, 400 and 450 V are shown. Injection (90 seconds) was performed by applying −120 V to the injection waste reservoir while maintaining all other reservoirs at ground potential. Separation occurred when the separation voltage ($V_s$) was applied to the high-voltage reservoir, 0.75 $V_s$ was applied to the sample and injection waste reservoirs, and the detection reservoir was maintained at ground. Samples were dissolved in the separation buffer (25 mM 2-(N-morpholino)ethanesulfonic acid, 1 mM $Cl^-$, pH 5.7). Detection was at +800 mV vs. the reference electrode. In FIG. 23 the access hole edge was 300 μm from the working electrode and electrophoretic separations of 1 mM dopamine at 600, 800, 1000 and 1200 V are shown. Injection and separation conditions were the same as described above.

In FIG. 22 where the spacing was 600 μm, the separation voltage ($V_s$) produced more interference than in FIG. 23 where the spacing was only 300 μm. Separations of dopamine at 300 V (60 V/cm) in the chip with a 600 μm spacing exhibited a flat baseline. Increasing $V_s$ in 50 V increments to 450 V (90 V/cm) resulted in decreased signal and a sloping baseline. For chips with the 300 μm hole-to-electrode spacing, the effect of $V_s$ was much less pronounced, permitting faster separations at higher $V_s$, increasing $V_s$ in 200 V increments resulted in only minor changes in the signal and baseline slope until $V_s$ reached 1200 V (240 V/cm). This effect of $V_s$ on the detection background is probably due to the difference between the potential in the buffer above the working electrode (determined by $V_s$) and the potential set at the working electrode by the potentiostat. Based on these results, we used a chip with 300 μm hole-to-electrode spacing and $V_s$=800 V for subsequent experiments.

To characterize these devices, we first performed capillary zone electrophoresis separations ($V_s$=800 V) and detection of neurotransmitters in a microfabricated CE chip with integrated electrochemical detection with the same conditions as in FIG. 23. The results are shown in FIG. 24 where the curves represent the following separations: A. Separation of 1 mM dopamine; B. Separation of 1 mM epinephrine; C. Separation of 1 mM catechol; and D. Separation of 330 μM dopamine (1), epinephrine (2), and catechol (3). Figure E shows peak height in separations as a function of injected concentration of dopamine (Δ), epinephrine (•) and catechol (□). Points on the plot represent the mean signal obtained in 3 duplicate separations. Analyses were carried out in uncoated channels to enable electroosmotic flow.

The numbers of theoretical plates in this separation were 21000, 17000 and 12000 for dopamine, epinephrine and catechol, respectively. The signal from each of the three components as a function of concentration was linear in the range from 10 to 1000 $\mu$M, as shown in FIG. 24E. Using the standard deviation of the signal (1.5 pA) from 55–70 seconds in a blank run, we determined limits of detection (signal-to-noise=2) of 3.7 $\mu$M for dopamine, 6.5 $\mu$M for epinephrine and 12 $\mu$M for catechol. The limit of detection of dopamine on-column, based on an estimated 18 pL injection volume was 66 attomoles, well within the expected range for electrochemical detection in CE.

The general applicability of these CE chips can be enhanced by developing electrochemically active labels and detecting other biomolecules. As a first step in this direction we have developed methods for separation and detection of DNA in microfabricated CE chips using an indirect electrochemical detection approach (F. Foret and P. Bocek, *Adv. Electrophoresis* 3, 273 (1989)) with the electrochemically active intercalation reagent, Fe(phen)$_3^{2+}$(phen=1,10-phenanthroline). The constant background current from free Fe(phen)$_3^{2+}$ in the separation buffer decreases when DNA-Fe(phen)$_3^{2+}$ complexes migrate through the detection region, so the passage of DNA is indicated by transient dips in the background current.

FIG. 25A shows separation of a ΦX174 HaeIII restriction digest (1 ng/$\mu$L), and FIG. 25B shows separation of a 1:200 dilution of a Salmonella PCR product (shaded) and 500 pg/$\mu$L ΦX174 HaeIII restriction digest. The current axis has been inverted in FIGS. 25A and 25B to display the electropherograms with the peaks pointing up. Injection (20 seconds) was performed by applying +120 V to the injection waste reservoir while maintaining the sample reservoir at ground and with the other two reservoirs floating. Separation was carried out by applying –800 V to the high-voltage reservoir while maintaining the detection reservoir at ground and with the other two reservoirs floating. Detection was at +800 mV vs. the reference electrode. The separation matrix contained 0.75% hydroxyethylcellulose, 40 mM Tris-acetate, 1 mM EDTA, 1 mM Cl$^-$, and 1 $\mu$M Fe(phen)$_3^{2+}$, pH=8.3. DNA samples were prepared in 0.1 mM Tris-Cl$^-$, 0.01 mM EDTA, pH=8.2. Channel surfaces were derivatized with linear polyacrylamide to suppress electroosmotic flow.

FIG. 25B further demonstrates that these microdevices have the sensitivity and resolution to size PCR products; a 159 bp amplicon from Salmonella was sized to 161 bp vs. the ΦX174 HaeIII peaks. Injection of 50 ng/$\mu$L ΦX174 HaeIII dissolved in electrophoresis buffer (under non-stacking conditions) yielded a signal of 190 pA for the 603 bp band. Based on an injection volume of 125 pL calculated from our previously estimated injection plug length of 330 $\mu$m, 700 fg (1.8 attomoles) of the 603 bp fragment were injected; therefore, the detection limit (signal-to-noise=2) was 28 zeptomoles for this fragment. These results indicate that CE chips with integrated electrochemical detection may be used for high-sensitivity biochemical assays that are competitive with traditional fluorescence detection methods. Furthermore, the development of direct labeling methods and multi-potential electrochemical detectors should enable multiplex electrochemical detection analogous to multi-wavelength fluorescence detection.

Development of various electrochemical labels for detection of chemical and biological analytes will pave the way to a host of applications including health care diagnostics and pathogen detection. Now that complete devices can be microfabricated, by improving the layout and packaging it should even be feasible to make chemical analysis microprocessors where the detection and computer circuitry are also integrated on-chip. With these improvement, integrated microanalysis devices should be capable of probing for biological signatures in a variety of challenging locations, including even extraterrestrial environments.

It should be apparent that the various thin film detector electrodes and thin film connections to the injection and separation channel can alternatively be made on the top cover plate which is then accurately positioned with respect to the channels.

Thus, there has been provided an improved integrated electrochemical detector on a microfabricated CE chip. This opens the way to a variety of interesting and useful analytes. For example, electrochemical detection on CE chips could be used for numerous analytes which are redox active. A microfabricated chip and electrochemical detector can be used for remote analysis of hazardous substances without the need for operator intervention. This invention is an important step towards complete integration of DNA and other analyses on microfabricated chips.

What is claimed is:

1. In a microfabricated capillary electrophoresis chip including a substrate with an elongated separation channel with conductive means at each end of the channel for applying a separation voltage along the channel, the improvement comprising an integrated electrochemical detector having at least one thin film working electrode extending into said separation channel at or very near one end of said separation channel adapted to detect molecules as they migrate past the thin film electrode after they have migrated down the channel, a portion of the thin film working electrode extending into said channel being very narrow in the direction of the separation electric field to minimize the effect of the electrophoresis voltage gradient which it senses along the channel and a reference electrode spaced 1–2000 $\mu$m from the thin film working electrode.

2. A microfabricated capillary electrophoresis chip as in claim 1 in which said channel is from 1–500 $\mu$m wide and 1–500 $\mu$m deep, said narrow end of the thin film working electrode is from 1–500 $\mu$m wide and the spacing between the ends of the thin film working electrode and reference electrode is from 1–500 $\mu$m.

3. A microfabricated capillary electrophoresis chip as in claim 1 in which the channel is from 1–2000 $\mu$m wide and 1–2000 $\mu$m deep, said narrow end of the thin film working electrode is from 1–2000 $\mu$m wide.

4. A microfabricated capillary electrophoresis chip as in claim 1 in which the channel at said one end transitions to a larger volume portion and said thin film working electrode and reference electrode are placed in or near the transition to a larger volume.

5. A microfabricated capillary electrophoresis chip as in claim 1 including a plurality of pairs of spaced thin film working electrodes disposed near said end of said channel to perform multiple potential electrochemical detection.

6. A microfabricated capillary electrophoresis chip as in claim 1 including thin film leads extending from said electrodes to the edge of said chip.

7. A microfabricated capillary electrophoresis chip as in claim 1 in which the channel transitions to a larger volume and said thin film working electrode is in said larger volume within 500 $\mu$m of the transition.

8. A microfabricated capillary electrophoresis chip as in claim 1 in which the channel transitions to a larger volume and said thin film working electrode is in said larger volume within 2000 µm of the transition.

9. A microfabricated capillary electrophoresis chip as in claim 1 including a plurality of spaced thin film working electrodes disposed near said end of said channel to perform multiple potential electrochemical detection.

* * * * *